US010485510B2

(12) United States Patent
Mansi et al.

(10) Patent No.: US 10,485,510 B2
(45) Date of Patent: Nov. 26, 2019

(54) PLANNING AND GUIDANCE OF ELECTROPHYSIOLOGY THERAPIES

(71) Applicant: Siemens Healthcare GmbH, Erlangen (DE)

(72) Inventors: Tommaso Mansi, Plainsboro, NJ (US); Tiziano Passerini, Plainsboro, NJ (US); Bogdan Georgescu, Plainsboro, NJ (US); Ali Kamen, Skillman, NJ (US); Helene C. Houle, San Jose, CA (US); Alexander Brost, Erlangen (DE); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 826 days.

(21) Appl. No.: 14/845,365

(22) Filed: Sep. 4, 2015

(65) Prior Publication Data

US 2016/0220311 A1    Aug. 4, 2016

Related U.S. Application Data

(60) Provisional application No. 62/109,249, filed on Jan. 29, 2015.

(51) Int. Cl.
*A61B 8/00* (2006.01)
*A61B 8/08* (2006.01)
*A61B 5/0402* (2006.01)

(52) U.S. Cl.
CPC .......... *A61B 8/4416* (2013.01); *A61B 8/0883* (2013.01); *A61B 8/463* (2013.01); *A61B 8/5215* (2013.01); *A61B 5/0402* (2013.01)

(58) Field of Classification Search
CPC ........ A61B 2034/104; A61B 2034/107; A61B 2090/374; A61B 34/10; A61B 5/0402; A61B 8/065; A61B 8/0883; A61B 8/12; A61B 8/4416; A61B 8/463; A61B 8/5215; A61B 8/5246; G16H 50/50
See application file for complete search history.

(56) References Cited

U.S. PATENT DOCUMENTS

| 2009/0254140 A1* | 10/2009 | Rosenberg | A61B 5/0422 607/17 |
| 2011/0144967 A1* | 6/2011 | Adirovich | G16H 40/63 703/11 |

(Continued)

OTHER PUBLICATIONS

[Aliev and Panfilov, 1996] R. R. Aliev and A. V. Panfilov. A simple two-variable model of cardiac excitation. Chaos, Solitons & Fractals, 7(3):293-301, Mar. 1996.

(Continued)

*Primary Examiner* — Mark D Remaly (57) ABSTRACT

A processor acquires image data from a medical imaging system. The processor generates a first model from the image data. The processor generates a computational model which includes cardiac electrophysiology and cardiac mechanics estimated from the first model. The processor performs tests on the computational model to determine outcomes for therapies. The processor overlays the outcome on an interventional image. Using interventional imaging, the first heart model may be updated/overlaid during the therapy to visualize its effect on a patient's heart.

12 Claims, 9 Drawing Sheets

(56) References Cited

U.S. PATENT DOCUMENTS

| | | |
|---|---|---|
| 2012/0087563 A1 | 4/2012 | Ionasec et al. |
| 2012/0296202 A1 | 11/2012 | Mountney et al. |
| 2013/0151221 A1* | 6/2013 | Chen .................. G06F 17/5018 703/9 |
| 2013/0197881 A1 | 8/2013 | Mansi et al. |
| 2013/0226542 A1 | 8/2013 | Rapaka et al. |
| 2014/0022250 A1 | 1/2014 | Mansi et al. |
| 2014/0296842 A1 | 10/2014 | Mansi et al. |

OTHER PUBLICATIONS

[Arsigny et al., 2007] Arsigny, Vincent, et al. "Geometric means in a novel vector space structure on symmetric positive-definite matrices." SIAM journal on matrix analysis and applications 29.1 (2007): 328-347.

[Audigier et al., 2013] Audigier, Chloé, et al. "Lattice Boltzmann Method for Fast Patient-Specific Simulation of Liver Tumor Ablation from CT Images." Medical Image Computing and Computer-Assisted Intervention—MICCAI 2013. Springer Berlin Heidelberg, 2013. 323-330.

[Chinchapatnam et al., 2008] Chinchapatnam, P. and Rhode, K.S. and Ginks, M. and Rinaldi, C.A. and Lambiase, P. and Razavi, R. and Arridge, S. and Sermesant, M. Model-based imaging of cardiac apparent conductivity and local conduction velocity for diagnosis and planning of therapy. IEEE TMI, 27(11), pp. 1631-1642, 2008.

[Georgescu et al., 2005] Georgescu B., Zhou X., Comaniciu D., Gupta A. Database-guided segmentation of anatomical structures with complex appearance. Proc. IEEE CVPR. 2005.

[Ionasec et al., 2010] Ionasec, Razvan Ioan, et al. "Patient-specific modeling and quantification of the aortic and mitral valves from 4-D cardiac CT and TEE." Medical Imaging, IEEE Transactions on 29.9 (2010): 1636-1651.

[Keener, 1991] Keener, J.P. An Eikonal-curvature equation for action potential propagation in myocardium, Journal of mathematical biology, 29(7), pp. 629-651, 1991.

[Leyva et al., 2014] Leyva, Francisco, Seah Nisam, and Angelo Auricchio. "20 Years of Cardiac Resynchronization Therapy." Journal of the American College of Cardiology 64, No. 10 (2014): 1047-1058.

[Mansi et al., 2012] Mansi, Tommaso, Ingmar Voigt, Bogdan Georgescu, Xudong Zheng, Etienne Assoumou Mengue, Michael Hackl, Razvan I. Ionasec, Thilo Noack, Joerg Seeburger, and Dorin Comaniciu. "An integrated framework for finite-element modeling of mitral valve biomechanics from medical images: Application to MitralClip intervention planning." Medical image analysis 16, No. 7 (2012): 1330-1346.

[Mitchell and Schaeffer, 2003] C. Mitchell and D. Schaeffer. A two-current model for the dynamics of cardiac membrane. Bulletin of mathematical biology, 65(5):767-793, 2003.

[O'Donnell et al., 2005] O'Donnell, T. and Dikici, E. and Setser, R. and White, R. Tracking and analysis of cine-delayed enhancement MR, Proc. MICCAI 2005, LNCS, pp. 692-700, 2005.

[Pernod et al., 2011] Pernod, E. and Sermesant, M. and Konukoglu, E. and Relan, J. and Delingette, H. and Ayache, N. A Multi-Front Eikonal Model of Cardiac Electrophysiology for Interactive Simulation of Radio-Frequency Ablation. Computers and Graphics, 53, pp. 431-440, 2011.

[Rapaka et al., 2012] S. Rapaka, T. Mansi, B. Georgescu, M. Pop, G.A. Wright, A. Kamen and D, Comaniciu. LBM-EP: Lattice-Boltzmann Method for Fast Cardiac Electrophysiology Simulation from 3D Images. Proc MICCAI 2012 (accepted for publication).

[Relan et al., 2011] Relan, J. and Chinchapatnam, P. and Sermesant, M. and Rhode, K. and Ginks, M. and Delingette, H. and Rinaldi, C.A. and Razavi, R. and Ayache, N. Coupled personalization of cardiac electrophysiology models for prediction of ischaemic ventricular tachycardia, Interface Focus, The Royal Society, 1(3), pp. 396-407, 2011.

[Sermesant et al., 2007] M. Sermesant, E. Konukoglu, H. Delingette, Y. Coudiere, P. Chinchapatnam, K. Rhode, R. Razavi, and N. Ayache. An anisotropic multi-front fast marching method for real-time simulation of cardiac electrophysiology. Proc. FIMH 2007, 9:160-169, 2007.

[Sermesant et al., 2012] Sermesant, Maxime, et al. "Patient-specific electromechanical models of the heart for the prediction of pacing acute effects in CRT: A preliminary clinical validation." Medical image analysis 16.1 (2012): 201-215.

[Ten Tusscher and Panfilov, 2006] Ten Tusscher, K. and Panfilov, AV. Cell model for efficient simulation of wave propagation in human ventricular tissue under normal and pathological conditions. Physics in medicine and biology, 51, pp. 6141, 2006.

[Tobon-Gomez et al., 2013] Tobon-Gomez, Catalina, Nicolas Duchateau, Rafael Sebastian, Stephanie Marchesseau, Oscar Camara, Erwan Donal, Mathieu De Craene et al. "Understanding the mechanisms amenable to CRT response: from pre-operative multimodal image data to patientspecific computational models." Medical & biological engineering & computing 51, No. 11 (2013): 1235-1250.

[Zheng et al., 2008] Zheng, Yefeng, Adrian Barbu, Bogdan Georgescu, Michael Scheuering, and Dorin Comaniciu. "Four-chamber heart modeling and automatic segmentation for 3-D cardiac CT volumes using marginal space learning and steerable features." Medical Imaging, IEEE Transactions on 27, No. 11 (2008): 1668-1681.

* cited by examiner

PLANNING AND GUIDANCE OF ELECTROPHYSIOLOGY THERAPIES

RELATED APPLICATIONS

The present patent document claims the benefit of the filing dates under 35 U.S.C. § 119(e) of Provisional U.S. Patent Application Ser. No. 62/109,249, filed Jan. 29, 2015, which is hereby incorporated by reference.

BACKGROUND

The present embodiments relate to cardiac modeling and therapy. Treatment of cardiac arrhythmias is a booming healthcare sector. However, cardiac electrophysiology (EP) therapies are often time consuming (e.g. ~3 h for an ablation of ventricular tachycardia) and with high number of non-responders (~30% for cardiac resynchronization therapy, ~50% for ablation therapy). The cardiac EP therapies require careful planning and advanced guidance systems for a patient-specific treatment.

One booming EP therapy is cardiac resynchronization therapy (CRT). An advanced pacemaker is placed to resynchronize a failing heart. The device paces the myocardium at the right ventricle endocardium (RV) and left ventricle (LV) epicardium, with given pacing intervals, to resynchronize the cardiac motion and hence re-establish the pumping efficiency of the organ. CRT is now a well-established therapy for heart failure. However, despite strict guidelines, ~30% of the treated patients do not respond.

BRIEF SUMMARY

The present invention provides for therapy planning and/or guidance using a generated heart model. A patient specific unified model is estimated from ultrasound images. A computational model of the heart is created using the unified model, including cardiac electrophysiology, mechanics, and hemodynamics. The computational model is used to test options and determine if a patient will respond to different therapies. The unified model and test results may be used during an interventional procedure as guidance.

In a first aspect, a method is provided where a processor acquires image data from a medical imaging system. The processor generates a first heart model from the image data wherein the first model includes a structural model, cardiac motion, and cardiac flow. The processor generates a computational heart model which includes cardiac electrophysiology, cardiac mechanics, and cardiac hemodynamics, estimated from the first model. The processor performs tests on the computational model to simulate outcomes for therapies, which can be used for planning. The processor displays the first model, computational model, and/or outcomes.

In a second aspect, a method is provided for therapy planning and guidance using a generated heart model. The method includes acquiring, from a medical imaging system, first data representing a cardiac structure of a patient. A processor derives from the first data, flow data, representing cardiac flow over time. The processor derives from the first data, motion data, representing cardiac motion over time. The processor generates a first unified heart model from the first data, flow data, and motion data. The processor acquires second data representing real-time cardiac structure of the patient. The processor overlaying the unified heart model with the second data.

In a third aspect, a system is provided for medical therapy and guidance. The system comprises a medical imaging system configured to acquire ultrasound data of a patient's heart, a processor, and a display. The processor is configured to derive a unified heart model from the ultrasound data; the unified heart model including cardiac structural, flow, and motion. The processor is configured to compute a computational model from the unified heart model, an electrophysiology model, and a hemodynamics model. The display is configured to display the computational heart model. The processor is further configured to simulate cardiac resynchronization therapy or other therapies on the computational heart model.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIGS. 6A, 6B, and 6C illustrate an example display of virtual cardiac resynchronization therapy.

DETAILED DESCRIPTION OF THE DRAWINGS AND PRESENTLY PREFERRED EMBODIMENTS

The multiplication of therapeutic alternatives and the associated increased complexity in therapy planning, delivery, and monitoring is creating a need for advanced image-based tools. Precisely quantifying patient physiology, computing surrogates of therapy outcome based on preoperative data, and guiding the clinician during therapy are the corner stone of personalized medicine. The embodiments described below include methods, systems, and instructions that combine ultrasound imaging, an interventional imaging system (e.g. angiography system or interventional MRI) and computational models for cardiac arrhythmias diagnosis and or cardiac electrophysiology (EP) therapy planning and/or guidance.

Ultrasound data representing a patient's heart is acquired from an imaging system. Ultrasound offers the possibility to visualize and quantify cardiac motion (strain), efficiency (ejection fraction), and/or cardiac flow. A unified model is generated from the information derived from the image data. Anatomical models of each cardiac chamber are estimated from the images to create a mesh model. Measurements based on the mesh model may be used together with certain physical and biomedical functions to simulate the blood flow as well as the interaction between the blood and anatomical structures of the heart.

A computational model is generated from the unified model. The mesh model and functional data of the unified model may be used along with electrocardiogram data to estimate the cardiac electrophysiology and the cardiac mechanics of a patient's heart.

The computational model is used to virtually test different therapies and gage potential outcomes. With the computational model, outcomes are computed to estimate changes in cardiac function due to the therapy. The computational model and outcomes may guide a clinician towards the optimal pacing site and pacing lead configuration through overlaid images. The unified heart model and outcomes derived from the virtually tested therapies are then used during interventional procedures. Multi-mode registration is employed to bring the real time interventional images and the unified model into an interventional coordinate system (e.g. through transthoracic echocardiogram (TTE) or transesophageal echocardiogram (TEE) probe detection). In this way, a user immediately sees the effects of a therapy on the cardiac function via the overlaid model information. The unified heart model and computational heart model may be updated during the intervention to see what the effects of the therapy on the patient are.

Figure 1:
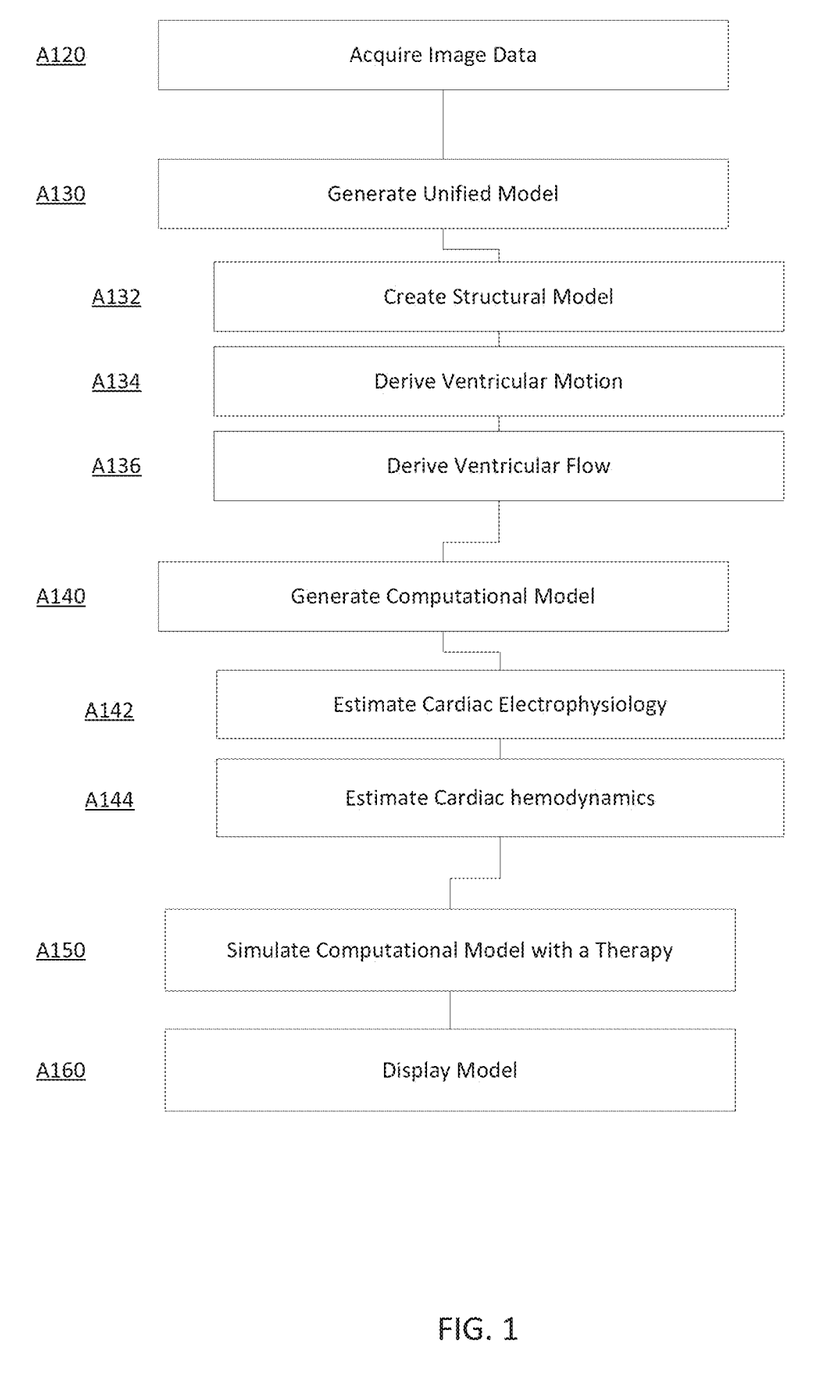
FIG. 1 is a flow chart diagram of one embodiment of a method generating a heart model to be used for therapy planning.

FIG. 1 is a flow chart diagram of one embodiment of a method generating a heart model to be used for therapy planning. The method of FIG. 1 is performed by the system of FIG. 8, a processor 20, a medical imaging system 16, or an interventional medical system 18.

Additional, different, or fewer acts may be provided. For example, steps A132, A134, and A136 are not required. A132, A134, and A136 include acts that add information to A130 where the unified model is generated. However, each of these may be considered subsidiary to A130 and may not be performed. Likewise, acts A142 and A144 are subsidiaries of act A140 and may or may not be performed. Acts A130 and A140 may include may include performing further acts depending on step A120 (image data) and whether additional acts such as collecting electrocardiogram or pressure data are performed.

The method is performed in the order shown or a different order. Act A130 (generating the unified model) and act A140 (generating the computational heart model) may include data or functionality estimated in Acts A132, A134, A136, A142, or A144. These acts may be performed in order or not in order and may be performed more than once. For example, act A140 may be performed multiple times as the cardiac mechanics (A142) are estimated. Each estimation may depend on parameters used and outputted by other acts. Likewise, an estimation of the cardiac mechanics and electrophysiology (A142, A144) may be performed multiple times as the unified model is adjusted.

Image Data Acquisition

In act A120, image data is acquired using a medical imaging system 16. Image data is data to be used to create an image (e.g., scan data) or is data for a displayed image (e.g., RGB data). Images may be in color or black and white.

In one embodiment, the image data is representative of a structure of a patient's heart. Images may be acquired with both the left ventricle (LV) and right ventricle (RV) visible. Images may be limited to a single ventricle or an area of a patient's heart. The image data may include data that represents an entire body or just a portion thereof. Any part of the heart may be represented. Other portions of the patient may be represented instead of the heart. Images acquired may be two dimensional (2D) or three dimensional (3D).

Figure 2:
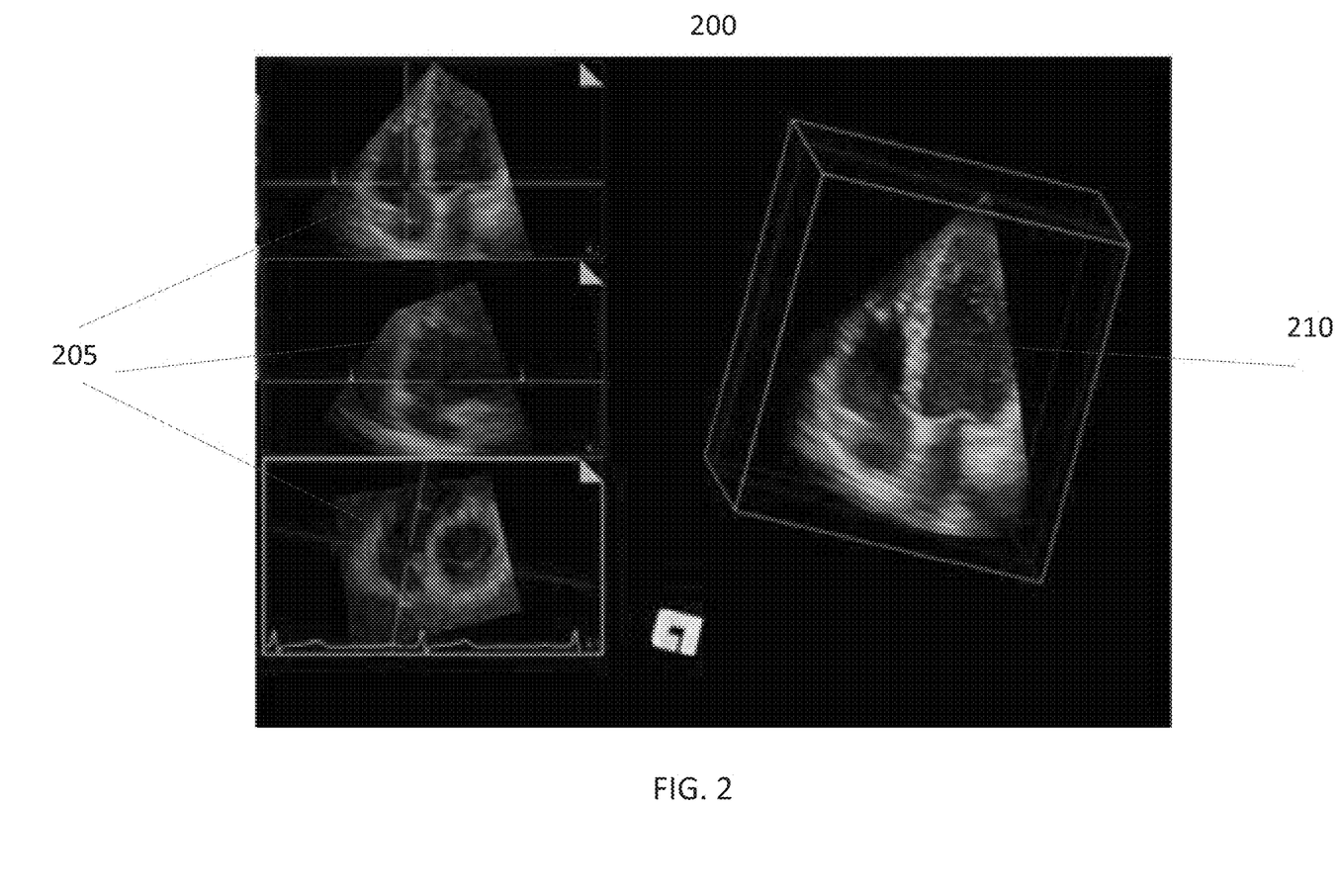
FIG. 2 illustrates examples of 3D ultrasound images.

FIG. 2 illustrates an example of acquired ultrasound images 200. In FIG. 2, both the left ventricle (LV) and right ventricle (RV) are visible in 2D images 205 along standard view planes. The image 205 may be acquired as 2D frames, but then may be rendered as a 3D image 210.

Images may be acquired over a period of time (2D+time or 3D+time) in order to track or detect movement. For example, multiple image frames may be acquired representing the heart over one or more cardiac cycles. Image data may be acquired at different times; e.g. over several visits or sessions.

Image data may be acquired using a single imaging system or multiple imaging systems. For example, image data may include both ultrasound and magnetic resonance imaging data. Image data may be acquired through different types of systems. For example, image data can be acquired from the patient using one or more medical imaging systems 16 including rotational angiography (DynaCT), computed tomography (CT), magnetic resonance imaging (MRI), ultrasound, positron emission tomography (PET), single photon emission computed tomography (SPECT), or other medical scan modality.

Rotational angiography (DynaCT) uses a C-Arm to acquire a 3D image. The C-Arm may be positioned relative to the body part in question so that this body part is in the isocenter between the x-ray tube and the detector. The C-Arm then rotates around that isocenter. The rotation takes a few seconds, during which a few hundred 2D images are acquired. A cone beam reconstruction is preformed to create a three-dimensional representation of the body part. The resulting voxel data may be used to create a multiplanar reconstruction.

A CT scan, also called X-ray computed tomography (X-ray CT) or computerized axial tomography scan (CAT scan), makes use of computer-processed combinations of many X-ray images taken from different angles to produce a three-dimensional representation of the patient.

MRI, nuclear magnetic resonance imaging (NMRI), or magnetic resonance tomography (MRT) are medical imaging techniques used in radiology to investigate the anatomy and physiology of the patient. MRI scanners use magnetic fields and radio waves to form images of the body.

PET is a nuclear medicine, functional imaging technique that produces a three-dimensional image of functional processes in the body of the patient. The system detects pairs of gamma rays emitted indirectly by a positron-emitting radionuclide (tracer) that is introduced into the body on a biologically active molecule. Three-dimensional images of tracer concentration within the body are then constructed by computer analysis.

SPECT is a nuclear medicine tomographic imaging technique using gamma rays. A gamma camera is rotated about a patient. The gamma camera captures photon emissions from a tracer in the patient.

Ultrasound imaging uses sound waves to image internal body structures. Techniques include transthoracic echocardiogram (TTE), transesophageal echocardiogram (TEE), and Intracardiac Ultrasound (ICE) among others. TTE is a non-invasive procedure where a transducer (or probe) is placed on the chest of the patient. Images are recorded using ultrasound data. For TEE, probe is passed through a patient's esophagus in order to be near the patient's heart. The probe may have an ultrasound transducer at the tip in order to provide imaging capabilities. ICE uses a catheter transducer elements. The catheter is threaded thru a vein in the groin and up into the heart.

Ultrasound scanning may be used to measure intensity of acoustic return, flow (e.g., Doppler), or other information. Diastolic function, fluid status, ventricular dyssynchrony may be measured.

Unified Model

Referring again to FIG. 1, at act A130, the processor 20 uses the acquired images from A120 to generate a unified heart model (unified ultrasound model or unified model) of the patient's heart. The unified heart model combines a structural model, with ventricular motion measurements mapped on the structural model, and ventricular flow measurements. The structural model may be derived from the image data. The ventricular motion may be derived from the structural model and/or the image data. The ventricular flow may be derived from the structural model and/or the ventricular motion and/or the image data (e.g. using Color Doppler imaging or phase-contrast MRI). The unified model may contain more or less information depending on the type and volume of image data collected at act A120.

At act A130, a structural heart model (or mesh) is created by the processor 20. The image data from act A120 may be in the form of image frames 205 illustrated in FIG. 2. Each image frame may contain data representing one or more chambers or components. The structural heart model may be created by first segmenting each component in the image data of the patient's heart. Individual models for one or more heart components, such as the left ventricle (LV) endocardium, LV epicardium, right ventricle (RV), left atrium (LA), right atrium (RA), mitral valve, aortic valve, aorta, and pulmonary trunk, are estimated from the image data. If the image data includes more than one image taken across a period of time, the images may be aligned or registered temporally. A detailed model may be created for each component and tracked across the multiple images or over time. Machine learning may be used to identify and track motion for each component.

In one embodiment, the processor 20 may use prediction based collaborative trackers (PCTs) to identify and track the components. Prediction based collaborative tracking (PCT) uses a low dimensional manifold to learn and then track a chamber or component of a heart over multiple image frames. Each training sequence contains a heart motion cycle which starts from the end-diastolic (ED) phase, passes through the end-systolic (ES) phase, and comes back to ED. The learning contains three steps. First the motion modes are learned using manifold learning and hierarchical K-means. Next, an ED detector is trained to locate the position of the object in the first frame. Finally, two boundary classifiers (one for ED and one for ES) are trained using the annotated sequences to delineate the boundary.

Once the components are identified and modeled, the processor 20 fuses the component models together to create a structural model. In order to integrate the individual component models, mesh point correspondences are established between connecting or overlapping models. The mesh point correspondences allow the models to be correctly aligned with respect to each other. If the components are detected in the same image, the components have a known spatial relationship. Otherwise the components models may be co-registered spatially and temporally using an anatomically consistent parameterization of the model. Temporal registration is achieved through temporal warping based on surrogate measurements like volume variation or ECG signal. Once co-registered, the combined model is computed. The structural model is generated by creating a closed, surface mesh including each component.

Figure 3A:
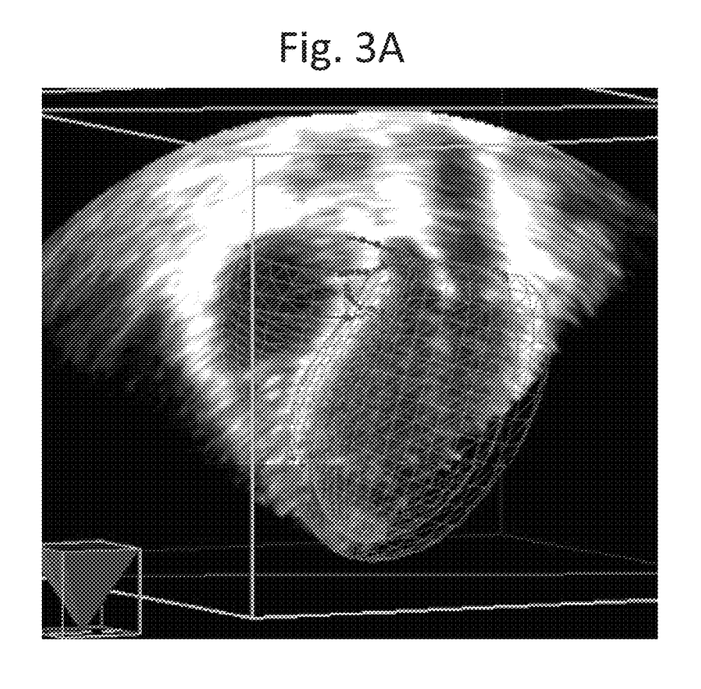
FIG. 3A illustrates an example of 3D ultrasound images.
Figure 3B:
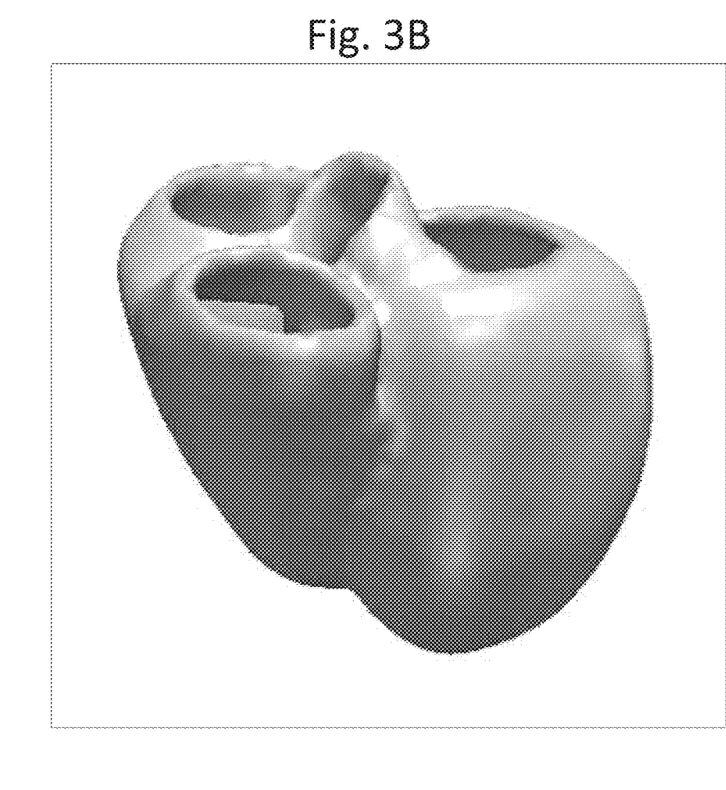
FIG. 3B illustrates a heart model based on the mesh of FIG. 3A.

FIGS. 3A and 3B illustrate a structural heart model with both LV and RV. FIG. 3A illustrates the heart model mesh overlaid on a two dimensional ultrasound image. FIG. 3B illustrates the structural heath model as a volumetric anatomical model.

At act A134 of FIG. 1, the processor 20 derives a model of ventricular motion from the structural model and imaging data. Modeling the ventricular motion may be based on the observed motion in the image data and/or using tissue information to predict motion. The structural model may exist in 4D (3D+time) and as such may exhibit motion over time. This motion may be tracked and fitted to the structural model. The motion of the patient's heart may also be modeled using a method such as myocardium strain tracking. Myocardium information and strain may be calculated by the processor 20 using speckle tracking, Doppler tracking, or other imaging techniques such as diffusion-weighted imaging or shear wave elasticity imaging.

Figure 5:
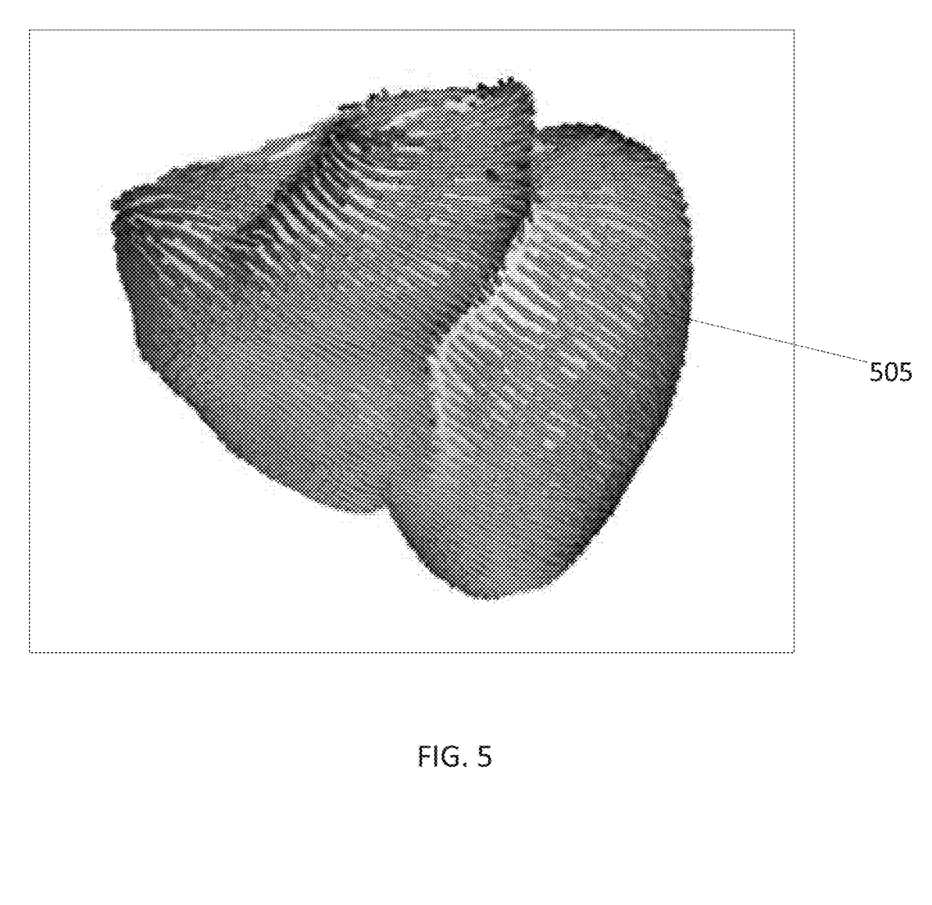
FIG. 5 illustrates a 3D heart model enhanced with myocardium fiber information.

FIG. 5 illustrates myocardium information 505 mapped to the structural model. Myocardium information 505 may be added to the structural model using data such as Doppler data. Doppler data may be processed and temporally registered to the structural heart model. Doppler data may be used to measure the movement of the myocardium tissue. The tissue data may be added to the structural model.

Additional methods may be used to identify and map myocardium data to the structural model. Diffusion-Weighted Imaging (DWI) may be used to detect tissue water diffusion rate. Water movements within the tissues are identified. Different tissues may exhibit different water movements and as such may be identified. DTI is a specific type of modeling of the DWI datasets.

Shear wave elasticity imaging (SWEI) may also be used to identify the type of tissue. SWEI uses shear acoustic waves to measure the elasticity of the heart. A resulting strain is then identified and mapped to the structural model.

The structural model including any myocardium information may be analyzed for motion using speckle tracking echocardiography (STE). STE analyzes the motion of tissues in the ultrasound images and structural model by using the naturally occurring speckle pattern in the myocardium or blood.

At act A136, the processor 20 quantifies the ventricular flow of the patient's heart. Using the image data, and/or structural model and/or ventricular motion, the processor 20 may detect and quantify flow patterns in the left and right ventricles. Doppler spectroscopy may also be used to measure the velocity of blood flow at specific regions. The volume change over time may be calculated. The amount, speed of blood flow, volume flow, maximum flow, minimum flow, and/or other flow measure is estimated or calculated for the patient from the image data. Computational fluid dynamics could also be used, given a moving structural model.

Figure 4:
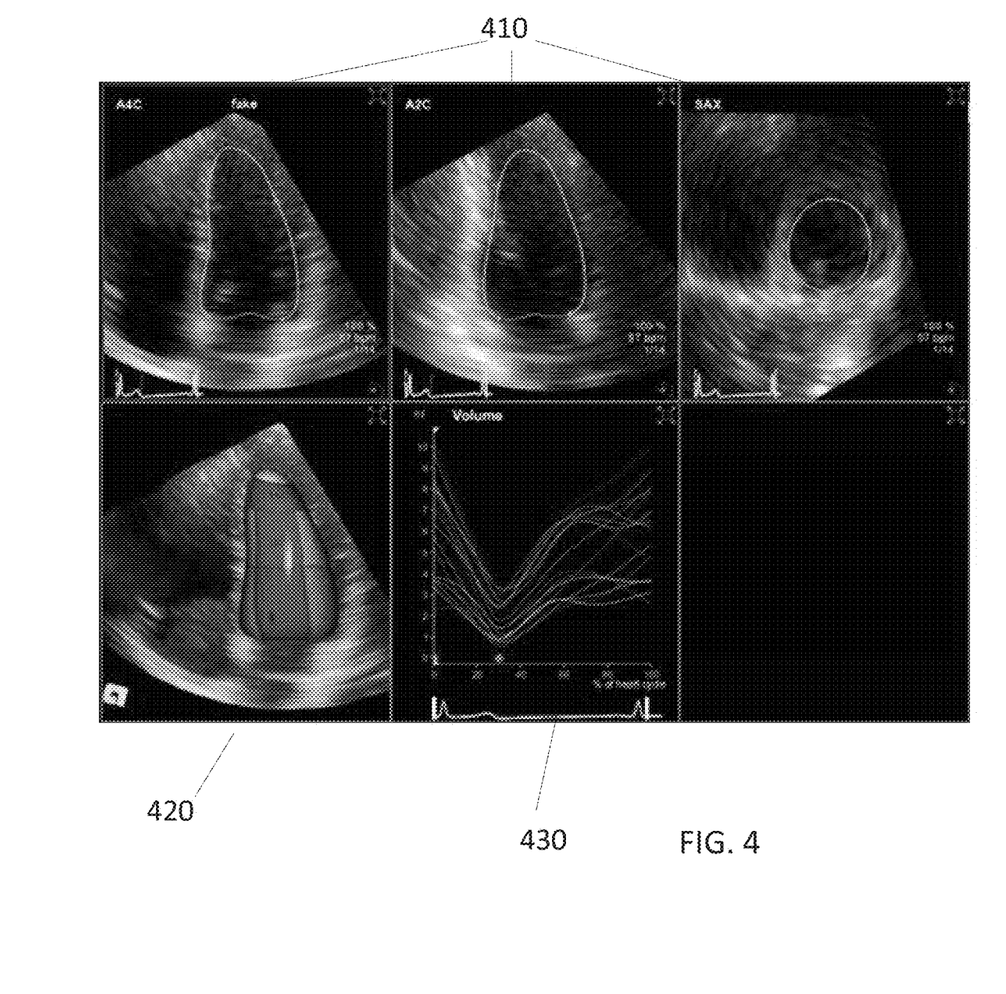
FIG. 4 illustrates an example of images from standard views and a measure of volume over time.

FIG. 4 illustrates 2D image scans 410, a 3D overlaid model 420 of the LV, and volume over time 430. The volume curves based on the 3D structural model are used to calculate ejection fraction and stroke volume.

Additional data may be added or included with the unified model. Further imaging data or other functional data may be acquired. Additional functionality may be derived from imaging data such as pumping motion or tissues identification (that may be used to better estimate motion or flow). As with the image data from Act 120, additional imaging data may be acquired from multiple imaging modes such as rotational angiography (DynaCT), CT, MRI, Ultrasound, PET, SPECT, among others. For instance, Delayed Enhancement MRI data could be used to segment myocardial scar and border zone, and map it to the unified heart model.

The unified heart models may be updated as necessary with either new patient data or additional functions. Each time a patient visits and gets tested or scanned, the image data may be acquired and used to update the unified model. The model could be updated also during an intervention, when interventional imaging (e.g. TEE ultrasound, interventional MRI) is acquired. Data collected from continuous monitoring devices may also be entered into the unified model. For example, a portable heart rate monitor may collect data throughout the day and night. Data may be updated or entered over a network. Data collected in one hospital or clinical setting may be combined with data collected previously or at a different hospital or clinic. The unified heart model may be accessed remotely or in a local setting.

Computational Heart Model

Referring back to FIG. 1, at Act A140, the processor 20 generates a computational heart model (computational model). The computational heart model is derived from the unified heart model from Act 130 including information representing the structural model, ventricular motion, and ventricular flow. The computational heart model further estimates patient's cardiac electrophysiology, cardiac mechanics and cardiac hemodynamics. These various models and estimates are registered temporally and spatially together in order to create a personalized model of a patient's heart. Adjusting the model in one area for example, the ventricular motion, will adjust the other models and estimates. For example, adjusting the inputs to the cardiac electrophysiology estimation may alter the cardiac mechanics and so forth.

At act A142, the processor 20 estimates the cardiac electrophysiology (EP) of the patient's heart. The cardiac EP estimate may be calculated using an existing model with parameters derived from the unified model or additional collected EP data. Models used may include Lattice-Boltzmann Method for Fast Cardiac Electrophysiology, biophysical models, phenomenological models, or Eikonal models.

EP is the electrical activity and the electrical pathways of a patient's heart. EP may be simulated based on the unified model using the ventricular flow, ventricular motion, and the myocardium fiber information. In one embodiment, additional data may be acquired to personalize the EP model. Using an electrocardiogram (ECG), EP data may be collected from a patient. In a conventional ECG, ten electrodes are placed on the patient's limbs and on the surface of the chest. The overall magnitude of the heart's electrical potential may be measured from twelve different angles ("leads") and is recorded over a period of time (usually 10 seconds). In this way, the overall magnitude and direction of the heart's electrical depolarization is captured at each moment throughout the cardiac cycle.

Using the ECG data and/or a 3D mesh of the structural model, the processor 20 estimates the parameters of a cardiac electrophysiology model, for instance the Lattice-Boltzmann Method for Fast Cardiac Electrophysiology (LBM-EP), to then calculate cardiac potentials over time. LBM-EP relies on the lattice-Boltzmann method to solve an anisotropic mono-domain equation of cardiac EP. LBM-EP may be used to solve any type of mono-domain cardiac electrophysiology models at near real-time. The domain is discretized on a Cartesian grid with a level-set representation of a patient's heart structure provided by the unified heart model. The cell model is calculated node-wise, while the transmembrane potential is diffused using Lattice-Boltzmann method within the domain defined by the level set. Any cellular model may be employed in the framework. In an embodiment, the Mitchell-Schaeffer model is used. Tissue anisotropy is considered, in which electrical activation is faster along the myocardium fibers than across. The model is coupled to a torso model for the computation of ECGs. Any model for mapping EP for a patient from any of the information of the unified model with or without additional EP or other data may be used. An inverse problem is then used to estimate the EP model parameters from the ECGs. Other EP data could be used, like invasive electrophysiology mapping.

Estimation of cardiac electrophysiology parameters (electrical conductivity and/or action potential duration) may be further refined by leveraging strain maps computed from the unified model. A first approach identifies lines of blocks from the strain map and uses the strain maps as prior knowledge to the EP estimation procedure. A second approach is to compute the local mechanical activation speed, and use the resulting map as first estimate of electrical conductivity, that is then refined using global ECG features. Alternatively, the strain information is used without the structural information to derive the computational model for the patient.

The computational model may also include additional estimates or models in order to better emulate the patient's heart. In an embodiment, a biomechanical model of the heart may be used to calculate the pumping function resulting from the electrical activation and the hemodynamics load calculated above. Two components are used: a passive component to capture the orthotropic nature of myocardium tissue (myocardium fibers and fiber sheets); and an active component that calculates the stress created by a myocyte during contraction.

Estimation of cardiac biomechanical parameters (e.g., active stress and/or tissue stiffness) may be further refined by leveraging the strain maps. The cost function includes the difference between the calculated and computed 3D strains. Using 3D image acquisition, the strain tensors may be directly compared in an embodiment using the log Euclidean framework. In this way, regional estimates are obtained. Furthermore, coupling the EP model and the image-derived motion and strain maps of the unified model, the location and extent of a scar may be inferred. Invasive endocardial mapping or body surface mapping may be used to identify border zone areas as akinetic areas (e.g., as quantified on the strain maps) with electrical activity.

At act A144, the processor 20 estimates a model of cardiac hemodynamics. In one embodiment, a lumped parameter model may be used, such as one pressure value being calculated per cardiac chamber. A lumped parameter model may use various parameters such as aortic pressure, systolic and diastolic blood pressure, blood flow, stroke volume, and/or heart rate. The parameters may be taken directly from or estimated from the unified model and/or imaging data. The lumped parameter model controls the cardiac phases according to arterial pressures, such as calculating using a 3-element Windkessel model, and atrial pressures, such as calculated using a lumped model of atrial contraction. In another embodiment, a full 3D computational fluid dynamics solver may be employed with fluid-structure interactions.

Estimation of cardiac hemodynamics parameters (arterial Windkessel parameters, atrial parameters) may be estimated using additional acquired image data such as image data from color Doppler, pulse-wave and continuous-wave Doppler. The flow directly provides pressure gradients and flow through valves, inputs to the models. These parameters and refinements may be updated and iteratively calculated by the processor 20 as data is added or modified.

Additional data may be added or included with the computational model. Further imaging data or other functional data may be acquired. As with the image data from Act 120, additional imaging data may be acquired from multiple imaging modes such as rotational angiography (DynaCT), CT, MRI, Ultrasound, PET, SPECT, among others. Additional or updated functional models may be added or included with the computational model.

The computational model may be updated as necessary with either new patient data or additional functions. Each time a patient visits and gets tested or scanned, the image data may be acquired and used to update the unified model. The unified model is then used to update the computational model.

Virtual Testing

Referring back to FIG. 1, at act A150, the processor 20 tests the computational model with a therapy option. Using a virtual representation (virtual model) of the computational model (e.g. rendered as a 3D volumetric model), different therapies may be tested their effect on cardiac function measurements viewed in order to achieve specific outcomes. Iteratively testing different setups or options may eventually create an outcome map. The outcome map may be used to assess disease severity and decide on an implant. The outcome map may be used for therapy planning such as the outcome map providing the user with additional physiological information and with surrogates of therapy outcome for patient selection but also therapy optimization. The outcome map may be used during intervention delivery, where the user overlay the outcome map on an interventional system for guidance towards the optimal therapy location.

The computational model (with the structural and functional data from the unified model) may be used by the processor 20 to provide a virtual model of patient's heart to a clinician or medical professional. The virtual model may be displayed using a display 24 either in 2D or 3D. The virtual model may be manipulated to alter the view of the model using a user interface. The virtual model may be run backwards or forwards if there is a time component. The virtual model may be in color or black and white. The virtual model may accessed using a virtual reality or augmented reality system. The computational model may then be used to test different therapies.

One type of therapy that may be tested is virtual cardiac resynchronization therapy (Virtual CRT). CRT (or biventricular pacing) may be helpful if the electrical impulses that control the heart muscle contraction and relaxation do not travel through the heart rapidly and evenly. The left ventricle may contract a fraction of a second after the right ventricle instead of simultaneously. CRT not only functions as a pacemaker but it re-coordinates (re-synchronizes) the beating of the two ventricles by pacing both simultaneously and specifically improving contraction of the left ventricle.

Using the patient-specific computational model, virtual CRT is performed by placing LV and RV leads on a virtual mesh model and applying electrical stimuli at these locations following a given pacing protocol. The pacing protocol provides frequency of each pacing, interval between LV and RV pacing, interval between first pacing lead and/or spontaneous depolarization. The protocols may be selected following the standard nomenclature of CRT devices (DDD, DDT, etc.) or freely set by a user. A library of devices may also be made available with their available protocols as listed in the manufacturer description for ease of use. More leads may also be simulated, along with more complex, adaptive pacing protocols. The electrical stimuli are applied as an additional localized electrical current in the electrophysiology model. The overall, patient-specific cardiac model is recalculated and parameters of the cardiac function derived from the model like QRS duration, electrical axis, QT duration, ejection fraction, stroke volume, or myocardium strain among others.

Virtual CRT may be performed either interactively (e.g., the user selects on the 3D model the position of the leads, the pacing protocol and re-calculates the model) or automatically. Automatic virtual CRT may test various options, allowing calculation of a range of possible outcomes based on the range of available protocol options. Virtual changes in cardiac electrophysiology, cardiac electrocardiogram (ECG), motion and hemodynamics are computed and displayed to the user.

Figure 6A:
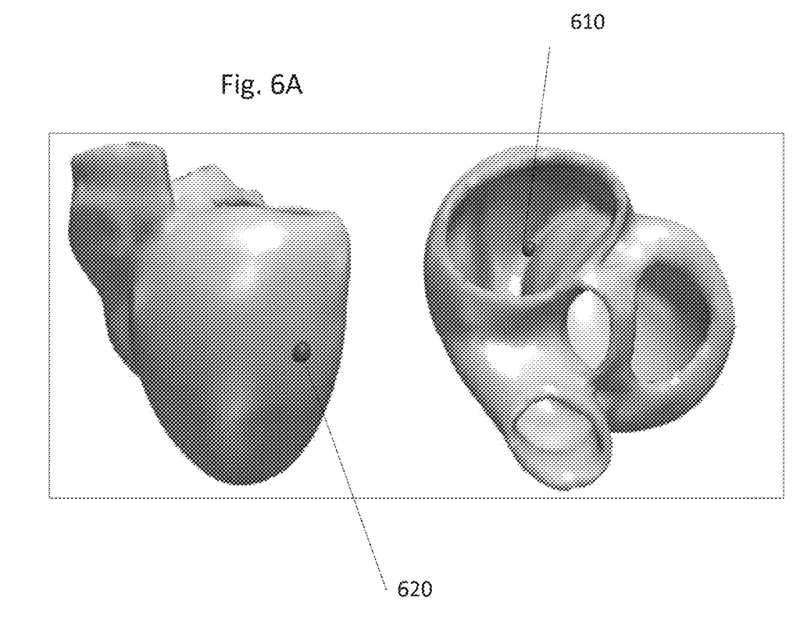
FIG. 6A shows how virtual device leads can be placed on the model.
Figure 6B:
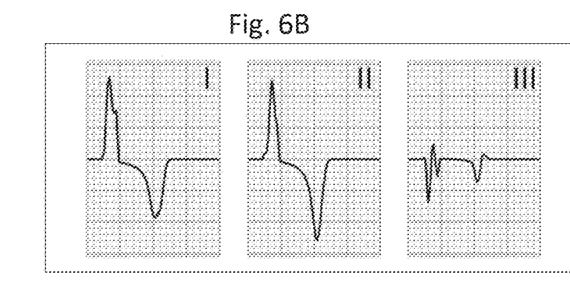
FIG. 6B illustrates a 12-lead ECG graph calculated using the model.
Figure 6C:
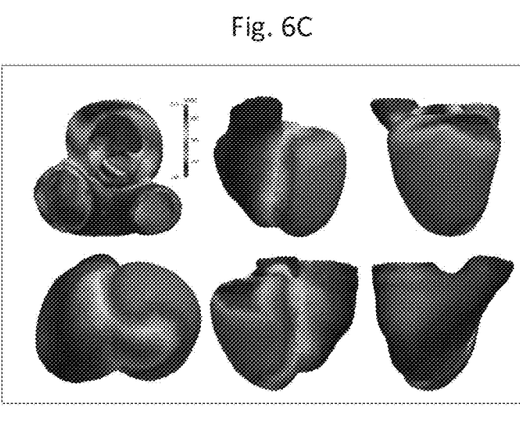
FIG. 6C illustrates an example of outcome map, where the color indicates the therapeutic improvement calculated by the model.

FIGS. 6A, 6B, and 6C illustrate an example display of Virtual CRT. In FIG. 6A, the LV 620 and RV 610 leads are positioned interactively by a user. The leads 610, 620 may be moved independently across the model by a user. The leads 610, 620 may also be moved using preset models or iteratively by the system. FIG. 6B illustrates an example of an ECG calculated by the computational model in response to the lead positions. FIG. 6C illustrates an Outcome map representing how optimal QRS vary based on LV lead position for a given pacing protocol. The intensity or color level indicates the magnitude change based on positioning.

Other issues, situations, and possible fixes that may be tested include valve repair, heart rhythm problems, lead location, pacing protocol, and other potential cardiac treatments.

Interventional Guidance

Referring back to FIG. 1, at act A160, the unified model, computational model and/or outcome map(s) are registered and overlaid on an interventional imaging system. The unified heart model, computational model and/or the outcome maps described in the previous sections may be calculated automatically offline based on pre-operative data, or online if interventional ultrasound and interventional 3D imaging of the heart are available. The unified model, computational model and/or outcome map(s) are then registered to an interventional system 18. The interventional system 18 may be a medical system such as an angiography system, an interventional MRI system, an interventional CT system, an EP mapping system, or an ultrasound system.

Figure 7:
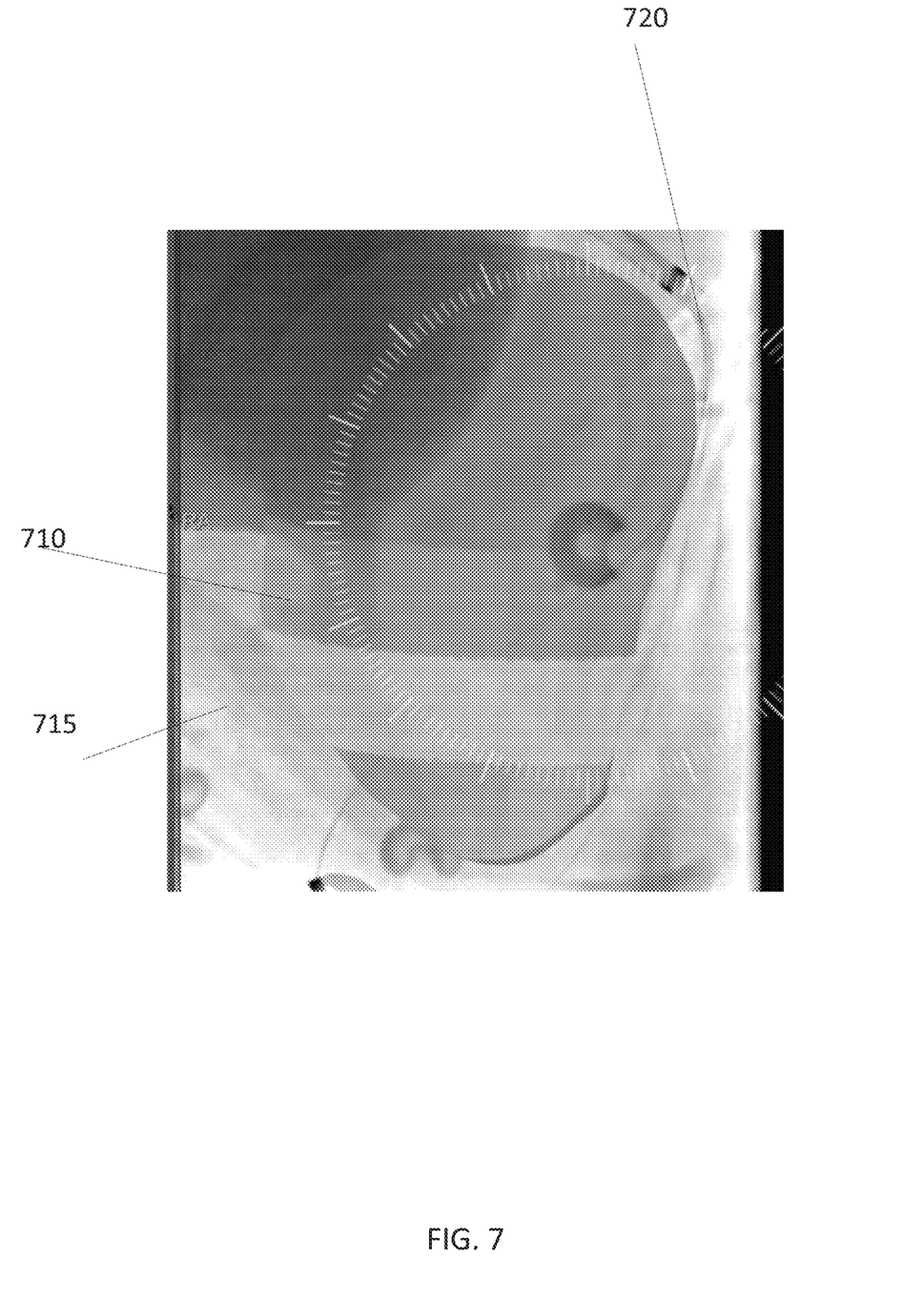
FIG. 7 illustrates an example image of a fluoroscopic overlay.

FIG. 7 illustrates an example image of a fluoroscopic overlay used by an interventional system 18. The unified model 710 is overload the interventional image 715. Using the overlaid image, a user may then be able to visualize the leads and catheter(s) 720 along with the outcome map, enabling the user to target the region with optimal outcome as identified by the model and outcome map.

In one embodiment, an interventional MRI system may be used to visualize the procedure. Therapeutic procedures may require real-time multi-slice acquisition and 3D display, and color highlighting of catheters. Real-time flow mapping using Doppler like imaging may be used. Non-ferrous materials may be used to the effect that ferrous materials have on the magnetic fields (and as such, the imaging). Alternative catheters, guidewires, coils, and other equipment may be used.

The unified heart model may be registered and overlaid on the interventional imaging system by using the spatial alignment of the unified heart model. The unified model and real-time imaging from the interventional imaging system may use a common coordinate system. Known specific points in the unified model and interventional imaging system may be aligned. If both images are not acquired simultaneously, a temporal alignment is determined by synchronizing the unified heart model with a concurrent ECG signal. The unified heart model may be display such that the unified model is actually a sequence of 3D models over a cardiac cycle. Accordingly, based on the ECG signal, the 3D model at a point in the cardiac cycle closest to each image frame may be selected. The unified heart model is then adjusted based on the concurrent 4D echo data to track the interventional imaging in the current frame, and the resulting unified heart model is overlaid on the interventional image frame.

In one embodiment, the unified heart model may be updated on demand to measure changes in the cardiac function as the therapy is delivered. A unified heart model is computed (from either preoperative or intra-operative images) and overlaid on the interventional imaging system. The unified heart model and the computational heart model are used together for therapy planning, the computational heart model providing the user with additional physiological information and with surrogates of therapy outcome for patient selection but also therapy optimization. The preoperative unified heart model is overlaid on the interventional imaging system during the intervention for therapy guidance (lead location, pacing protocol). The unified heart model is calculated directly during the intervention for therapy guidance (lead location, pacing protocol) but also direct quantification of real-time effects on the cardiac function (e.g. quantify live changes in myocardial motion, blood flow, etc.). The computational heart model is computed and continuously updated to guide the clinician towards the optimal therapy (lead location, pacing protocol), guided by updated therapy outcome surrogates. The computational heart model is updated at each patient visit (follow-up or disease monitoring), providing updated model-based parameters and outcome surrogates for predictive monitoring.

Figure 8:
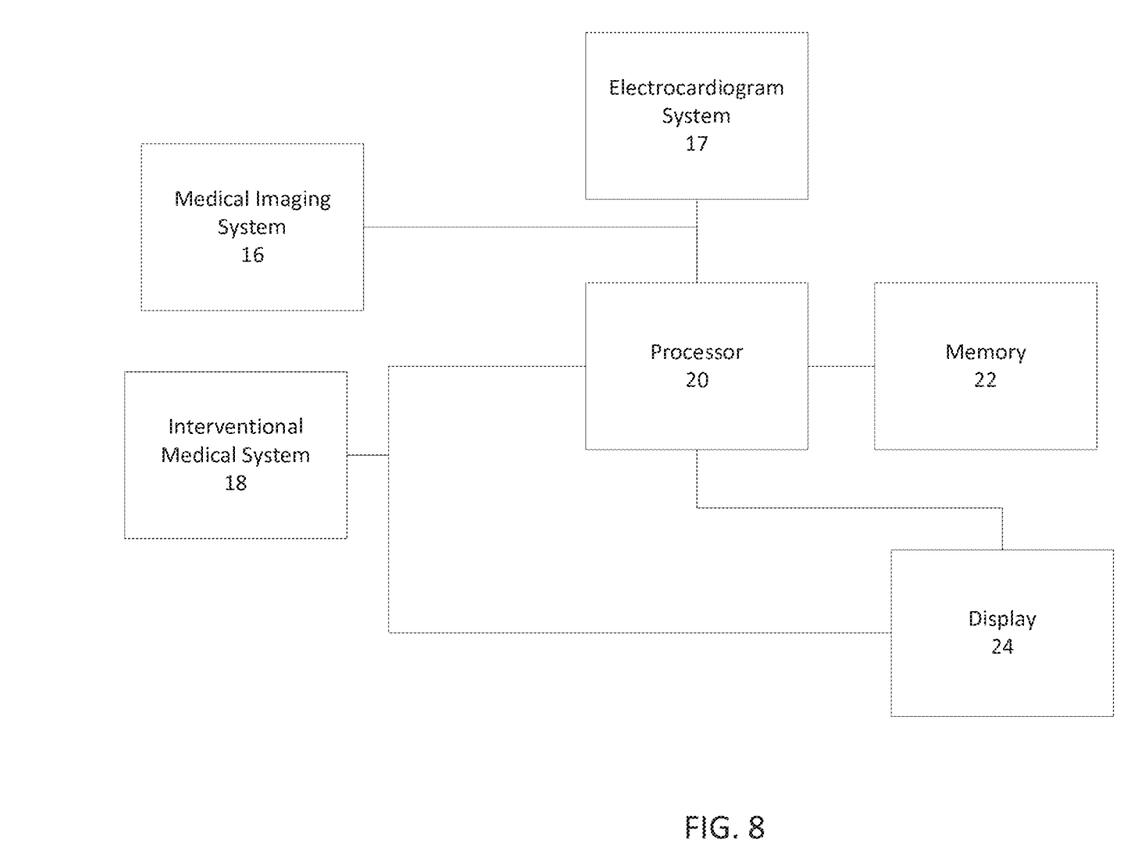
FIG. 8 illustrates an example system used to plan and guide electrophysiology therapies from multi-modality images.

FIG. 8 illustrates an example system used to generate a computational heart model used to plan and guide electrophysiology therapies. The system includes a medical imaging system 16, an electrocardiogram system 17, an interventional system 18, a processor 20, a memory 22, and a display 24. Additional, different, or fewer components may be provided. For example, a network or network connection is provided, such as for networking with a medical imaging network or data archival system. As another example, the electrocardiogram system 17 may be included within the interventional system 18. As another example, a user interface is provided. In yet another example, the medical system 16 is not provided. The data representing the patient is obtained from the memory 22, possibly from a previous visit. The medical imaging system 16 may be included within the interventional system 18. The processor 20 and memory 22 may be included within the medical imaging system 16 or the Interventional system 18.

Figure 9:
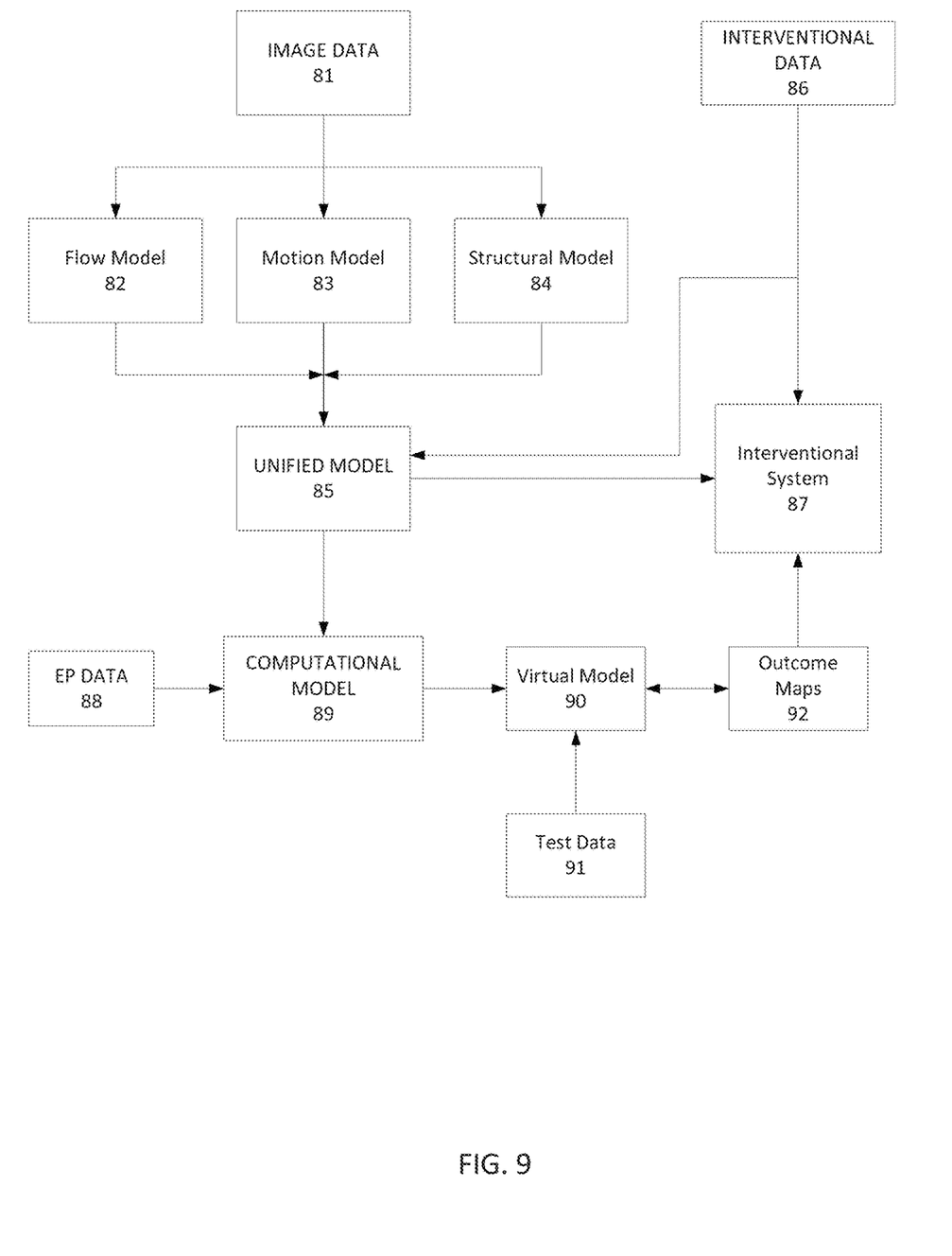
FIG. 9 illustrates a work flow of an example embodiment.

The system implements the method of FIG. 1 or a different method. For example, the work flow of FIG. 9 is implemented. The system of FIG. 8 is described below in the context of implementing the work flow of FIG. 9.

Imaging data 81 is acquired from the imaging system 16. The medical imaging system 16 is configured by stored settings and/or by user-selected settings to collect data regarding a patient or a portion of the patient. The medical imaging system 16 may use such technologies as rotational angiography (DynaCT), CT, MRI, Ultrasound, PET, SPECT, among others. The collection may occur by transmitting and receiving or by receiving alone. By positioning relative to the patient, aiming, and/or detecting, the anatomy is scanned. For example, the heart is scanned. The scanning may be repeated to scan the patient over time, such as scanning to acquire multiple frames of scan data representing the patient at different times throughout a physiological cycle. By scanning over time, changes in the anatomy due to the cycle may be captured. Other information, such as from other anatomy, may or may not be acquired as well.

The processor 20 derives, calculates, generates, or estimates various models from the image data. These include the flow model 82, the motion model 83, and the structural model 84 (segmentation) of the patient's heart. The processor 20 computes a unified heart model 85 from the models and/or estimated outputs from the models. The unified model 85 and other data is stored in memory 22.

The processor 20 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for creating a patient specific computational heart model for therapy planning and guidance. The processor 20 is a single device or multiple devices operating in serial, parallel, or separately. The processor 20 may be a main processor of a computer, such as a laptop or desktop computer, or may be a processor for handling some tasks in a larger system, such as in an imaging system. The processor 20 is configured by instructions, design, firmware, hardware, and/or software to be able to perform the acts discussed herein.

The processor 20 and memory 22 may be part of the medical imaging system 16 or other system. Alternatively, the processor 20 and/or memory 22 are part of an archival and/or image processing system, such as associated with a medical records database workstation or server. In other embodiments, the processor 20 and/or memory 22 are a personal computer, such as desktop or laptop, a workstation, a server, a tablet, a network, or combinations thereof.

EP data 88 is collected from the patient using the EKG system 19 or an invasive mapping system. The processor 20 uses the EP data 88 and the unified model 85 and/or pressure data to create a computational model 89 for the patient. The computational model 89 may be able to model cardiac electrophysiology and/or mechanics. The computational model 89 is displayed as a virtual model 90 that may be tested with various therapies. The virtual model 90 is then tested using test data 91, such as lead placement, to calculate outcomes maps 92. During a procedure, an interventional system 18, 87 overlays the unified model 85 with the outcome maps 92 and interventional data 86 to guide a user.

An interventional system 18 may be 18 may be a medical system such as an angiography system, an interventional MRI system, an interventional CT system, an EP mapping system, or an ultrasound system.

The memory 22 is a graphics processing memory, video random access memory, random access memory, system memory, cache memory, hard drive, optical media, magnetic media, flash drive, buffer, database, combinations thereof, or other now known or later developed memory device for storing scan data. The memory 22 is part of the imaging system 16, a computer associated with the processor 20, a database, another system, a picture archival memory, or a standalone device.

The memory 22 may store processed data. For example, filtered scan data, image processed data, segmentation, created mesh, surface model, volume model, template model, material properties, model parameters, and other collected data. The memory 22 may also store additional data, e.g. EP data, or other collected data that is used in the computational model.

The memory 22 or other memory is alternatively or additionally a computer readable storage medium storing data representing instructions executable by the programmed processor 20 for generating a unified model, a computational model, and testing therapies. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts, or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method comprising:
acquiring, from a medical imaging system, image data representing at least one chamber of a patient's heart;
generating, using a processor, a first model from the image data, wherein the first model includes a structural model, cardiac motion, and cardiac flow;
generating, using the processor, a computational model, wherein the computational model includes cardiac electrophysiology, cardiac biomechanics, and cardiac hemodynamics estimated from the first model;
generating a virtual model including the computational model rendered as a 3D volumetric model;
placing at least one left ventricle lead on the virtual model;
placing at least one right ventricle lead on the virtual model;
applying an electrical stimulus at least one of the left ventricle lead and right ventricle lead;
simulating a response of the virtual model;
generating an outcome map of the response; and
displaying the outcome map in features of the virtual model.

2. The method of claim 1 wherein the image data is one or more 3D ultrasound images.

3. The method of claim 1 wherein generating a first model comprises:
creating the structural model of the patient's heart using the image data;
estimating the cardiac motion from the image data;
quantifying the cardiac flow from the image data; and
mapping the cardiac motion and cardiac flow to the structural model.

4. The method of claim 3, wherein creating a structural model comprises:
segmenting the image data into one or more chambers of the patient's heart;
creating a mesh model for each chamber using the segmented image data; and
fusing the mesh models together.

5. The method of claim 1, further comprising:
acquiring, from an interventional imaging system, an interventional image;
registering the outcome map to the interventional imaging system;
registering the first model to the interventional imaging system; and
overlaying at least one of the first model, the computational model, or the outcome map on the interventional image.

6. The method of claim 5, further comprising:
acquiring real time data from the interventional imaging system; and
updating the first model and virtual model with the real time data.

7. The method of claim 1, further comprising:
acquiring electrophysiological data from an electrophysiology system, wherein the electrophysiological data is used to estimate the parameters of the cardiac electrophysiology model.

8. The method of claim 1, wherein the cardiac electrophysiology is computed using a Lattice-Boltzmann method.

9. The method of claim 1, wherein cardiac hemodynamics is computed using a lumped parameter model coupled with the electromechanical model.

10. The method of claim 1, further comprising:
acquiring, from a medical imaging system, updated image data that covers the at least one chamber of a patient's heart; and
generating an updated first heart model.

11. A method comprising:
acquiring, from a medical imaging system, first data representing a cardiac structure of a patient;
deriving, from the first data, flow data representing cardiac flow over time;

deriving, from the first data, motion data representing cardiac motion over time;
generating a unified heart model from the first data, flow data, and motion data;
acquiring, from an interventional imaging system, second data representing real-time cardiac structure of the patient;
overlaying the unified heart model on the second data;
generating a virtual model including the unified heart model rendered as a 3D volumetric model;
placing at least one left ventricle lead on the virtual model;
placing at least one right ventricle lead on the virtual model;
applying an electrical stimulus at least one of the left ventricle lead and right ventricle lead;
simulating a response of the virtual model;
generating an outcome map of the response; and
displaying the outcome map in features of the virtual model.

12. The method of claim 11, wherein the second data is magnetic resonance image data.

* * * * *